Figure 1:
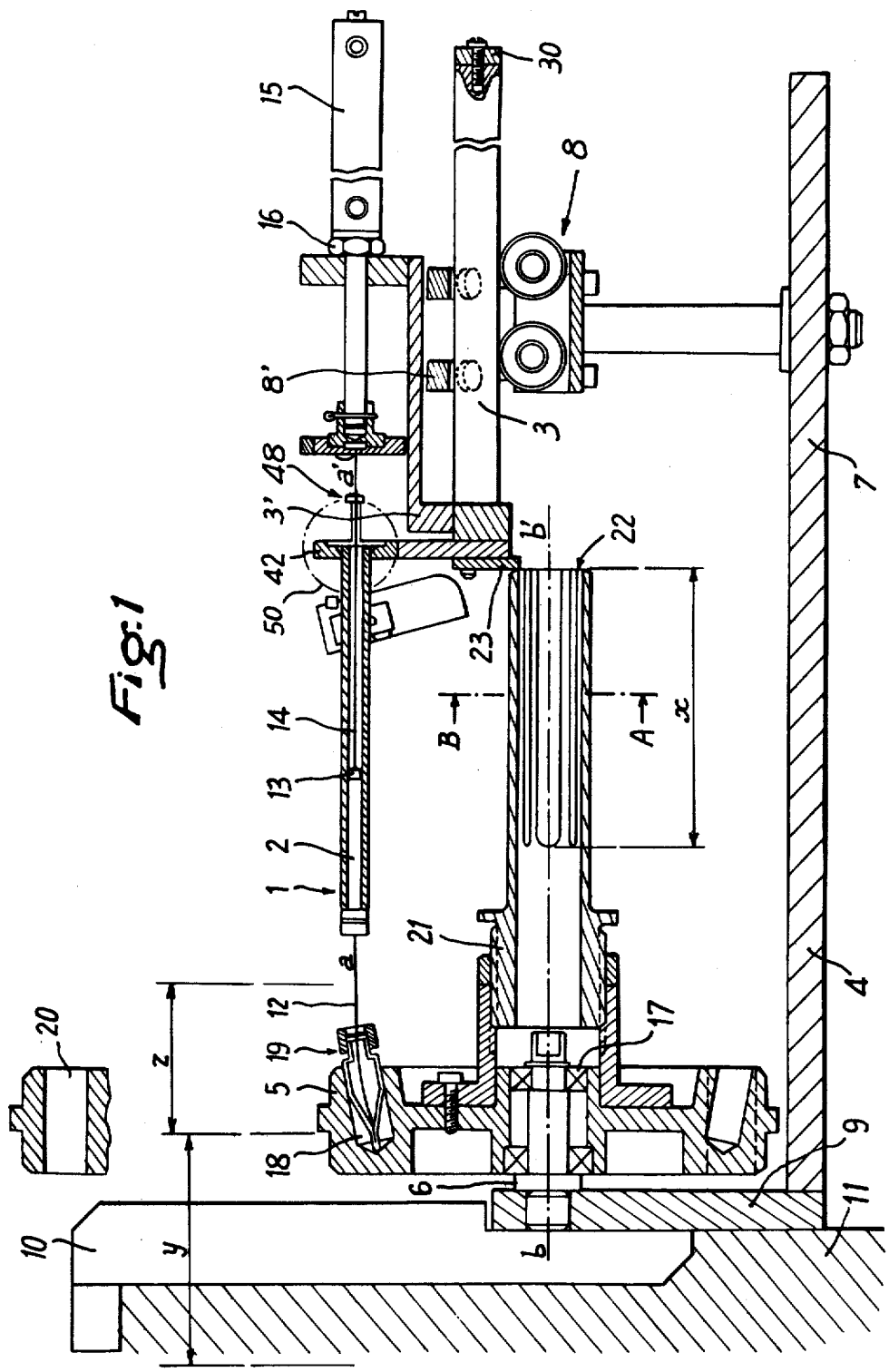

United States Patent [19]

Baldin et al.

[11] 4,038,874

[45] Aug. 2, 1977

[54] DEVICE FOR THE INSERTION OF SAMPLES INTO A CHROMATOGRAPHY COLUMN

[75] Inventors: Pierre Baldin, Bizanos; Albert Brocco, Jurancon; Jean-Paul Winstel, Lescar, all of France

[73] Assignee: Societe Nationale Elf Aquitaine (Production), Courbevoie, France

[21] Appl. No.: 679,095

[22] Filed: Apr. 21, 1976

[30] Foreign Application Priority Data

Apr. 24, 1975 France .................................. 75.12749

[51] Int. Cl.² .......................................... G01N 1/14
[52] U.S. Cl. .............................. 73/422 GC; 73/423 A; 222/144
[58] Field of Search .................... 23/259, 253 R; 73/422 GC, 423 A; 222/144

[56] References Cited

U.S. PATENT DOCUMENTS

| 3,096,653 | 7/1963 | Martin et al. ............... 73/422 GC |
| 3,190,731 | 6/1965 | Weiskopf ..................... 23/259 X |
| 3,508,442 | 4/1970 | Lightner et al. .............. 23/259 X |
| 3,550,453 | 12/1970 | Lightner et al. ............. 73/422 GC |
| 3,713,777 | 1/1973 | Auphan et al. ............... 23/253 R X |
| 3,754,443 | 8/1973 | Harris, Sr. et al. ........... 73/422 GC |
| 3,918,913 | 11/1975 | Stevenson et al. ........ 73/422 GC X |

*Primary Examiner*—Joseph Scovronek
*Assistant Examiner*—Arnold Turk
*Attorney, Agent, or Firm*—Brisebois & Kruger

[57] ABSTRACT

This invention concerns a device for inserting samples into a chromatography column.

The device comprises a syringe mounted on a carriage, a sample-holder consisting of a circular plate and a control system linking the syringe and sample-holder. The plate and syringe axes are parallel, the axis of the sample-holder cell is at an angle of at least 10° to the horizontal, each cavity for a sample-holder cell is followed in turn by an aperture and a cavity for a cell containing a rinsing liquid, and a control system is provided so that during injection of the sample into the chromatography column, the syringe needle passes through the aperture.

The proposed device is specially adapted for chromatographic analysis of samples in the trace form.

7 Claims, 6 Drawing Figures

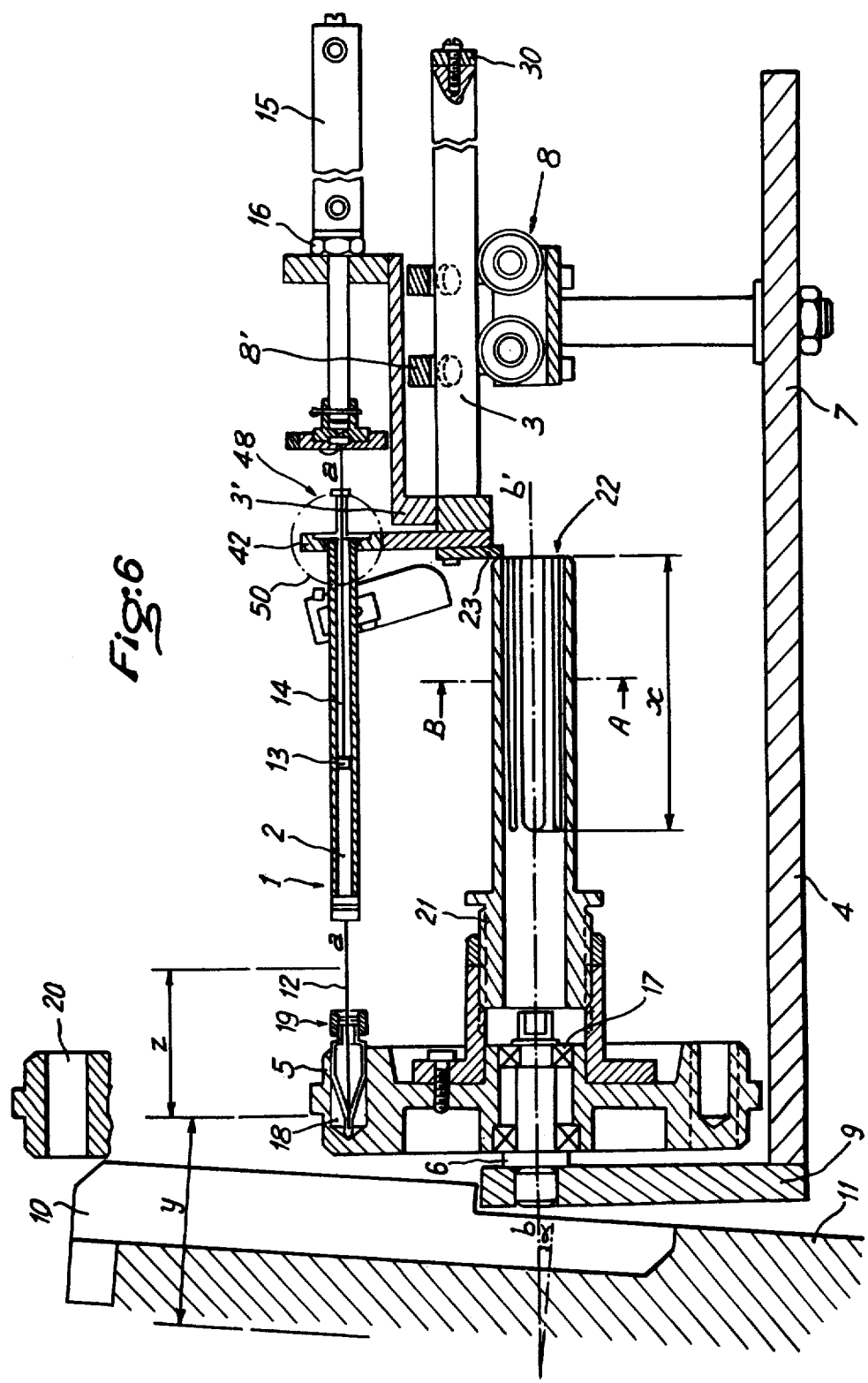

DEVICE FOR THE INSERTION OF SAMPLES INTO A CHROMATOGRAPHY COLUMN

This invention relates to a device allowing samples to be inserted, at given intervals of time, into a chromatography column, particularly for gas-phase chromatography.

Gas chromotagraphy is normally used to analyse mixtures of organic substances, such as natural hydrocarbons, which contain molecules of widely differing sizes, with boiling points that extend over a very wide range of temperatures. Definition of the temperature gradient of the elution programme results from a compromise between the amount of resolution required (which is largely an inverse function of the temperature gradient) and the total duration of analysis, which governs its cost. In normal practice, gas-phase chromatographic analysis of natural hydrocarbons requires 2 to 3 hours, thus allowing eight analyses in 24 hours with the sample appliance — hence the usefulness of a sample-insertion device allowing continuous functioning.

Various automatic devices exist for inserting liquid samples into the injection chamber of a chromatographic column at regular intervals of time. In such devices, the syringe takes the sample and fills up in a vertical position, then tips over 90° and injects it in a horizontal position.

Vertical extraction has been adopted so far because it is the only way of ensuring effective recuperation of liquid in existing sample cells. In such automatic devices, the syringe is tipped over by means of a complicated, cumbersome mechanism.

This invention overcomes these difficulties by combining the functioning of a horizontal syringe, mounted on a carriage which imparts only translational movements to the syringe, with the functioning of a distributor plate which revolves on an axis parallel to the syringe axis, and the perimeter of which contains cells for samples and for the rinsing product, these cells being tapered, and at an angle such that the syringe, because of the flexibility of the needle, can collect most of the sample.

This device for inserting samples into a chromatography column comprises:

- a syringe consisting of a cylindrical body communicating with a needle and fixed to a carriage which can travel parallel to the syringe axis, and to a piston, the rod of which is controlled by a jack on the moving carriage;
- a sample-holder consisting of a circular plate, which can revolve step by step on its axis, with cavities in this plate, opening on the side of the plate facing the syringe, the centres of these openings being located on a circle with the same axis as the plate, and with cells containing either a sample or a rinsing product fitted into these cavities;
- a control system linking rotation of the sample-holder plate to travelling movements of the syringe needle and of the whole syringe, in order to perform a repeated cycle of operations comprising extraction of a sample, its injection into the chromatography column, and rinsing-out of the syringe.

This device is characterized by the fact that the plate and syringe axes are on the same vertical plane, and cavities are located so that when the central point of their opening is in the vertical plane of the plate and syringe axes and aligned with the syringe axis, the axis of the cavity is at an angle of at least 10° to the horizontal, and that each cavity for a cell containing a sample is followed in turn by an aperture through which the syringe needle can pass and by a cavity for a cell containing a rinsing liquid.

In this device, the control system linking rotation of the sample-holder plate to travelling movements of the syringe needle and of the whole syringe comprises a cam integral with the syringe stand and a slotted drum coaxial and integral with the circular sample-holder plate, containing the same number of slots as the plate has apertures for the syringe needle to pass through, the circular plate axis being parallel to the syringe axis.

Wherever samples are available in very reduced volumes, cells containing them are tapered, ending in a cone with a half-angle at the vertex of approximately 10°.

In one recommended embodiment, the axes of the circular plate and syringe are horizontal, and the axes of the cavities in the plate form the generating lines of a cone with the same axis as the plate, these cavity axes being at an angle of at least 10° to the plate axis, and the vertex of the cone being situated, in relation to the plate, on the side opposite the syringe side.

In another embodiment, the axes of the plate and syringe are at an angle of at least 10° to the horizontal, and the axes of the cavities in the plate are parallel to these plate and syringe axes.

Figure 2:
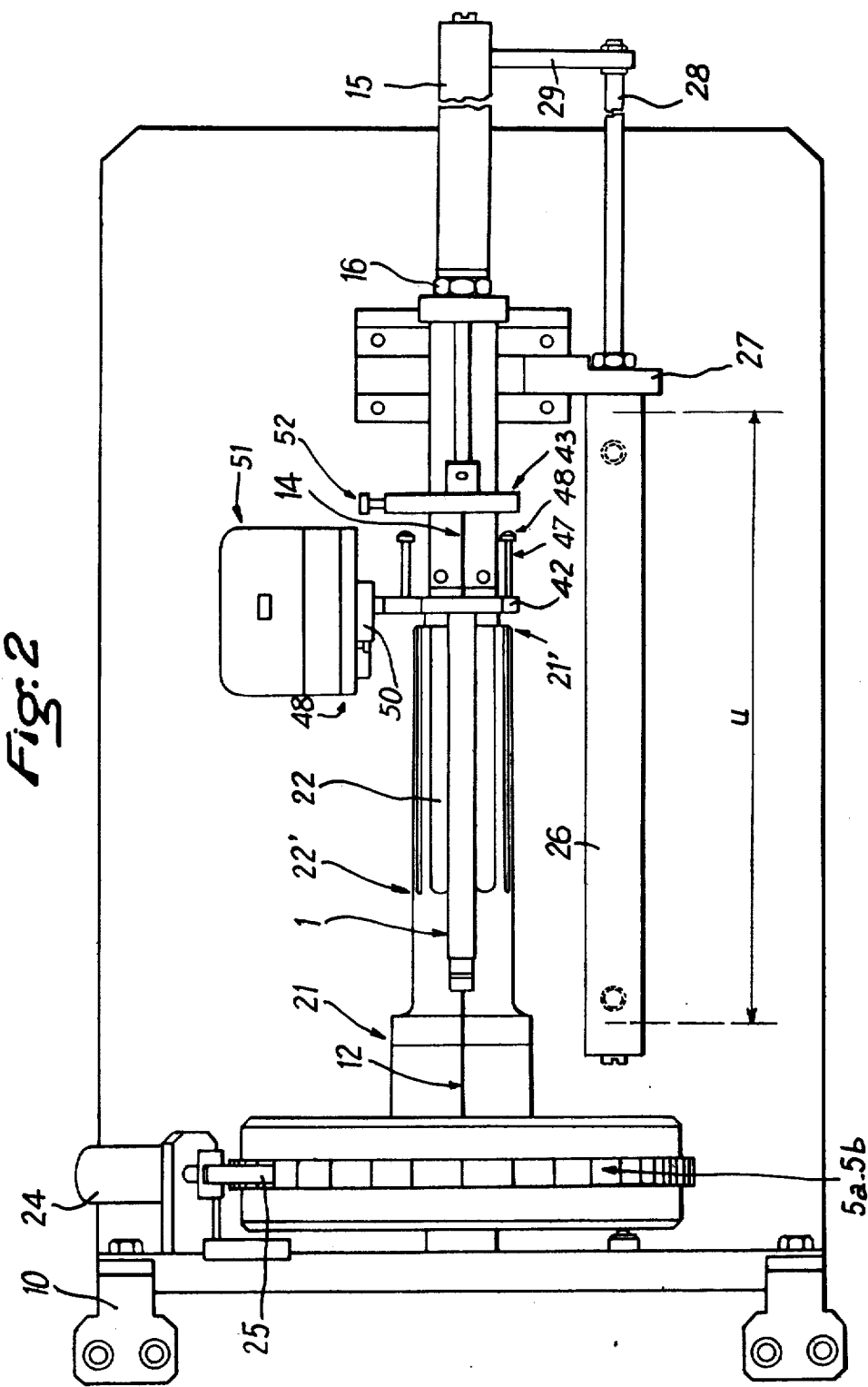
Figure 3:
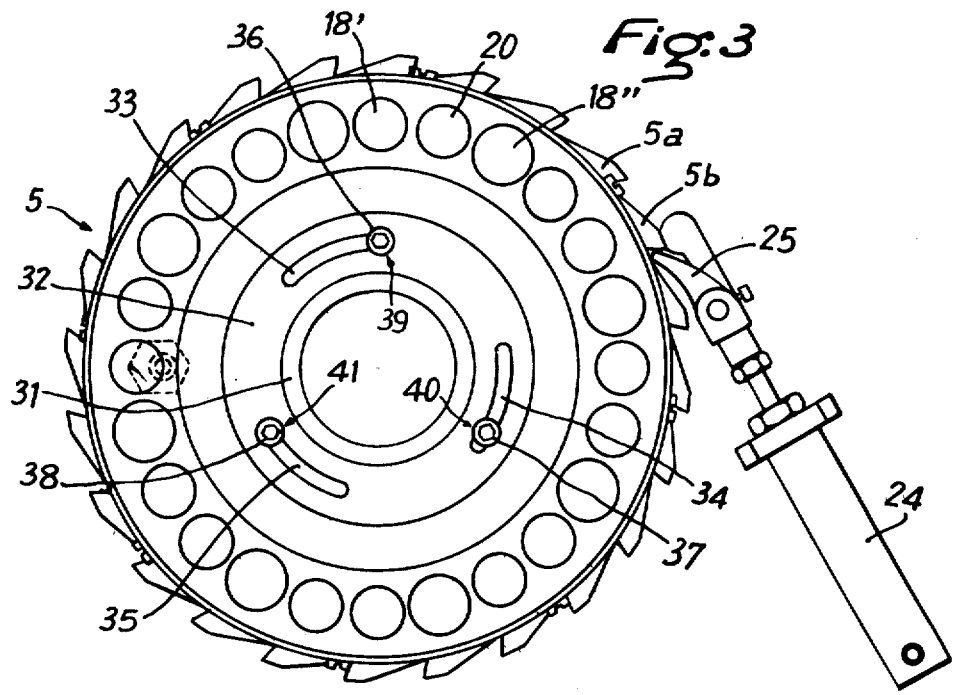
Figure 4:
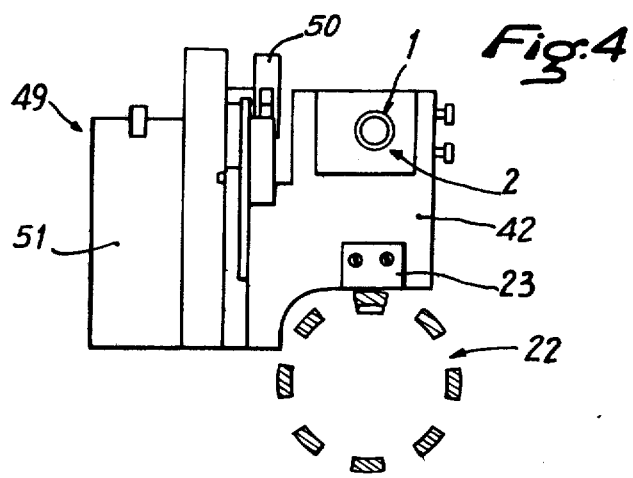
Figure 5:
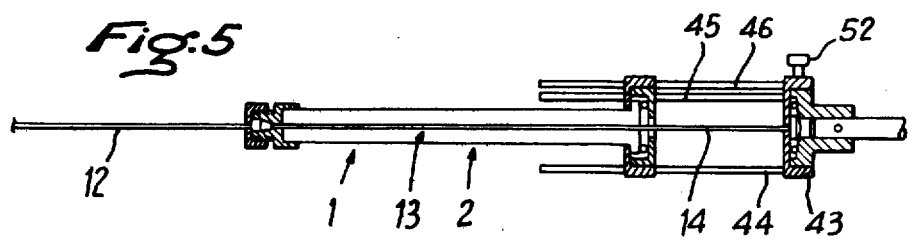

The invention is illustrated more comprehensibly, without in any way being confined to, the following embodiment, accompanied by the following figures :

FIG. 1: Cross-section of a first embodiment of the device taken in a vertical plane;

FIG. 2: View of the device from above;

FIG. 3: View of the sample-holder plate and its driving mechanism;

FIG. 4: View of carriage along the syringe axis;

FIG. 5: View of syringe.

FIG. 6: Cross-section of a second embodiment of the device taken in a vertical plane.

FIG. 1 shows a syringe 1, comprising a cylindrical body 2 with a horizontal axis ($a\ a'$), fixed to a carriage 3, which is capable of travelling movements, parallel to the syringe body axis, in relation to a support 4. The syringe co-operates with a circular sample-holder plate 5, the axis of which ($b\ b'$) is parallel to the syringe body axis ($a\ a'$). The plate 5 can pivot on a coaxial shaft 6, which is attached to the support 4.

The support 4 contains a horizontal part 7 to which is attached to the slide-rail or similar system 8 along which the carriage 3 moves. It also contains a vertical part 9, to which is attached the shaft 6 on which the circular plate 5 pivots. Finally, it contains a device 10 allowing it to be attached to the frame of the chromatographic column 11 (these can consist for example of metal brackets with bolts).

The cylindrical body 2 communicates with an injection needle 12, which is attached to the end of the body by means known in the previous art. A piston 13 moves inside the body 2, attached to one end of a rod 14, the other end of which is connected to the piston of a jack 15, the body 16 of this jack being connected rigidly to the syringe body 2.

In figure 1, the circular sample-holder plate 5 is mounted on the shaft 6 by means of two ball-bearings 17.

The side of the circular plate 5 facing the syringe contains, located at regular intervals round a circle concentric with the plate, on the one hand the openings of cavities 18 cut into the mass of the plate to allow cells 19, containing either samples 18' or rinsing products 18", to be placed there, and on the other hand apertures 20, through which the needle 12 can pass, in order to inject the sample into the chromatography column.

These cavities 18 are cylindrical in shape, their axes being at an angle of approximately 15° to the plate axis (b b'), and forming the generating lines of a cone, the vertex of which lies on the plate axis (b b'), opposite the side of the plate facing the syringe.

The sample-holder cells 19 are tapering, ending in a cone with a half-angle at the vertex of approximately 10°.

The apertures 20 are in the shape of cylindrical holes with axes parallel to the plate axis (b b'), being therefore horizontal.

Each cavity for a sample-holder cell round the circle concentric with the plate is followed by an aperture, which in turn is followed by a cavity for a cell containing a rinsing product.

When chromatography analysis operations each take 3 hours, continuous functioning of the analysis apparatus for a 24-hour period is obtained by providing eight sample-holder cells; continuous functioning for a 48-hour period is obtained by providing 16 sample-holder cells.

The circular plate 5 is integral with a coaxial drum 21, containing longitudinal slots 22, adapted to receive a cam 23 integral with the syringe carriage 3. The length (x) of these slots is equal to the distance (y) that the needle 12 must travel to allow it to penetrate into the chamber feeding the chromatography column 11.

The same parts as in FIG. 1 appear in FIG. 2, seen from above.

It shows the jack 15 which controls movement of the syringe-piston rod 14.

The circumference of the circular plate 5 contains a number of asymmetrical teeth 5a, 5b, etc, like the teeth of a clockwork escapement mechanism. The number of teeth is the same as the total number of cavity openings and apertures on the side of the plate 5 facing the syringe.

A jack 24, attached to the support 4, controls a pawl 25 which moves the teeth, causing the plate 5 to rotate step by step.

A jack 26, the axis of which is parallel to the syringe axis, comprises a barrel 27 integral with the support 4 and a piston rod 28, the end of which is fixed rigidly to the carriage 3 by means of a member 29. The stroke of this jack 26 is equal to the combined total of the distance (y) that the needle 12 must travel to enable it to penetrate into the chamber feeding the chromatography column and of the distance (z) that it must travel between its starting position and the position in which it extracts a sample from the cell 19.

The jack 26 causes the carriage to move from a back position, defined by engagement of a part 3' of the carriage 3 with a part 8' of the support 8, and two forward positions, defined respectively by engagement of the cam 23 with the end 21' of the drum 21, and by engagement of this cam with the bottom 22' of a slot 22. FIG. 3 shows a front view of the circular sample-holder plate 5 and its driving mechanism, showing the inlet 18' of a cavity for a sample-holder cell, followed by the inlet 20 of an aperture through the plate, followed in turn by the inlet 18" of a cavity for a cell containing a rinsing product.

The drum 21 (not shown here) is integral with a ring 31, containing a flat flange-shaped part 32, provided with three apertures 33, 34 and 35, located at equal distances round a circle concentric with the flange 32. Each of these apertures occupies a segment of approximately 20°. Pins 36, 37 and 38 pass through each of these apertures respectively, one end being screwed into the plate 5 and the other end carrying tightening nuts 39, 40 and 41 respectively. Adjustment of the position of these pins in the apertures allows the position of the drum to be adjusted in relation to the plate 5.

FIG. 4 is a view of the carriage 3, taken along the syringe axis, from a cross-section of the drum 21 along line A B. This figure shows, on the section of the drum 21, the eight slots 22 along which the cam 23 slides when the syringe carriage moves from the position for extracting a sample from a cell to the position for injecting it into the the chamber feeding the chromatography column. In this figure, the cam 23 is against the end of the drum 21, corresponding to one of the two positions for extracting a sample or for rinsing.

The cam 23 is integral with a plate 42 fixed to the body 2 of the syringe 1 and also to the carriage and body 16 of the jack 15.

FIG. 5 is a longitudinal section of the syringe 1, constructed along lines known in the prior art. It shows the cylindrical body 2 within which the piston 13 moves, being attached to one end of the rod 14, the other end of which is attached to the piston of a jack 15 by means of a connecting member 43. Rods 44, 45 and 46 are attached to this member 43, parallel to the syringe axis, and sliding in guide-passages in the syringe body 2.

FIGS. 1, 2 and 4 show various subsidiary parts of the syringe 1.

Rods 47 are attached to the plate 42, parallel to the syringe axis, and ending in stops 48, on which the member 43 rests when the piston 13 is in the position corresponding to graduation 0 on the syringe.

Also to this plate 42 is attached a mechanism 49 controlling extraction of the sample, comprising a cam 15 driven by a micro-motor 51, or a motor geared very low, and resting on a roller 52 integral with member 43.

The throw of the cam 50 is equal to the stroke that the piston 13 must make for extraction of the sample.

The device for inserting samples into a chromatography column, as described above, operates as follows.

To begin with, the chromatography column is in the waiting position, and the carriage 30 on the device is in its rear position, the syringe facing a cell containing the rinsing product, rinsing having taken place.

The jack 24, acting through the pawl 25 on a tooth 5b, causes the plate 5 to rotate by 1/24 of a turn, so that the opening of a cavity 18 containing a sample-holder cell comes into position facing the syringe.

The syringe 1, actuated by the jack 26, moves forward in such a way that the needle 12 perforates the rubber cover of the cell, comes up against the cell wall and, being flexible, follows this wall, which is at an angle of approximately 15° to the horizontal, stopping at the end of its movement a few millimetres from the bottom of the cell (this limit position is governed by the contact between the cam 23 and the end 21' of the drum 21).

The jack 15 controlling movements of the syringe piston 13 causes it to make a forward and backward movement 10 times, so as to remove air bubbles from the needle. The final position of the piston 13 is in the forward position, corresponding to graduation 0 on the syringe.

Pressure in the jack 15 is released. The cam 23 thereupon comes into position against the roller 52 integral with the member 43 and, under the effect of the micrometer 51, causes movement of the member, and therefore of the piston 13, corresponding to the volume of sample required. Volumes as small as $10^{-6}$ litre are common.

Under the effect of the jack 24, the sample-holder plate 5 revolves by 1/24 of a turn, bringing the aperture 20 in line with the syringe axis.

The jack 26 again moves the carriage 3 forward. The cam 23 is facing a slot 22 on the drum 21, and the carriage stops in its forward limit position when the cam 23 comes into contact with the bottom 22' of the slot. During this movement, the syringe needle 12 pierces the rubber cover or septum of the chamber feeding the chromatography column.

Under the effect of the jack 15, the sample is injected, whereupon the chromatographic analysis programme begins to function.

The jack 26 moves the carriage into its back limit position.

The jack 24 causes the plate 5 to revolve by 1/24 of a turn, which brings the aperture of the cavity 18', holding a cell containing a rinsing product, into the syringe axis.

The jack 26 moves the carriage forward, so that the cam 23 comes up against the end 21' of the drum 21. During this movement, the point of the needle penerates the cell containing the solvent.

The jack 15 performs several forward and back movements to rinse out the syringe.

The jack 26 moves the carriage into the back limit position.

The advantages of the device described above lie in the simplicity of movements of the syringe, which consist solely of translational movements, and in the rigorous nature of the operation, ensuring elimination of air bubbles before the product for analysis is sampled, and also the recovery of minimal quantities of product, because of the combination of the shape of the cell and of its position in space during extraction, as well as thorough rinsing of the parts of the syringe that have been in contact with the sample.

In an alternative embodiment illustrated in FIG. 6, the axis of the plate and the syringe are at an angle of at least 10° to the horizontal and the axis of the cavities in the plate are parallel to the plate and syringe axis. As shown in FIG. 6, α represents the angle of displacement of the axis of the plate (bb') with respect to the horizontal.

These advantages ensure total reliability for the feeding of a chromatographic analysis appliance operated in a continuous manner.

What is claimed is:

1. In a device for the insertion of samples into a generally vertical chromatography column comprising:
    a sample holder comprising a plate mounted to rotate about an axis transverse to said column, said plate defining a plurality of cavities arranged in a ring about said axis,
    said chromatography column being located on one side of the sample holder,
    a syringe mounted on the other side of said sample holder in a position such that said cavities become successively aligned with said syringe as said plate rotates, said syringe comprising an elongated hollow body, a needle at one end of said body, and a piston mounted in said body, and both said piston and said body being mounted for translational movement parallel to said axis, and
    the improvement according to which at least some of said cavities are adapted to receive a sample cell while others are holes passing through said plate, the axis of rotation of the plate and the path of translational movement of said syringe lie in the same vertical plane, and the center line of a cavity aligned with said syringe, taken in a vertical plane containing said axis, is at an acute angle of at least 10° to the horizontal,
    and said device comprises control means for correlating the rotation of said plate to the translational movements of said syringe and piston in order to carry out a cycle of operations including the withdrawal of a sample from a cell in one of said cavities and the injection of said sample through one of said holes into said column.
2. Device as claimed in claim 1 in which the axis of rotation of said plate and the path of translation of said syringe lie at about 10° to the horizontal and the center lines of said cavities are parallel to said axis and path.
3. A device as claimed in claim 1 in which said syringe body is mounted on a carriage and said control means comprises a cam integral with said carriage and a slotted drum coaxial with and integral with said plate, and containing the same number of slots as the plate has holes.
4. A device as claimed in claim 1 in which said cavities are grouped in series of three, one of which contains a sample cell, one of which is a through hole, and one of which contains a rinsing cell.
5. Device as claimed in claim 1 in which the axis of rotation of said plate and path of translation of said syringe are horizontal and the center lines of said cavities lie in a conical locus, and wherein the axis of said conical locus is the axis about which said plate rotates and the vertex of said locus is located in the other side of said plate from said syringe.
6. A device as claimed in claim 5 comprising cells fitting into said cell-receiving cavities, said cells having tapered ends with a vertex angle of about 20°.
7. A device as claimed in claim 5 in which said needle is flexible.

* * * * *